(12) United States Patent
Yoo (10) Patent No.: US 7,901,344 B2
(45) Date of Patent: Mar. 8, 2011

(54) METHODS OF REDUCING SURGICAL COMPLICATIONS IN CANCER PATIENTS

(75) Inventor: John Yoo, London (CA)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

(21) Appl. No.: 12/118,167

(22) Filed: May 9, 2008

(65) Prior Publication Data

US 2008/0306431 A1 Dec. 11, 2008

Related U.S. Application Data

(60) Provisional application No. 60/917,434, filed on May 11, 2007.

(51) Int. Cl.
*A61N 5/00* (2006.01)
(52) U.S. Cl. .............................. 600/1; 424/532
(58) Field of Classification Search .................. 600/1–8
See application file for complete search history.

(56) References Cited

U.S. PATENT DOCUMENTS

| | | | |
|---|---|---|---|
| 5,165,938 A | 11/1992 | Knighton | |
| 5,318,782 A | 6/1994 | Weis-Fogh | |
| 5,585,007 A | 12/1996 | Antanavich et al. | |
| 5,788,662 A | 8/1998 | Antanavich et al. | |
| 6,054,122 A | 4/2000 | MacPhee et al. | |
| 6,063,297 A | 5/2000 | Antanavich et al. | |
| 6,117,425 A | 9/2000 | MacPhee et al. | |
| 6,214,338 B1 | 4/2001 | Antanavich et al. | |
| 6,323,146 B1 | 11/2001 | Pugh et al. | |
| 6,398,972 B1 | 6/2002 | Blasetti et al. | |
| 6,585,992 B2 | 7/2003 | Pugh et al. | |
| 6,649,072 B2 | 11/2003 | Brandt et al. | |
| 6,790,371 B2 | 9/2004 | Dolecek | |
| 6,811,777 B2 | 11/2004 | Mishra | |
| 6,905,612 B2 | 6/2005 | Dorian et al. | |
| 6,960,352 B2 | 11/2005 | Noujaim et al. | |
| 7,011,852 B2 | 3/2006 | Sukavaneshvar et al. | |
| 7,094,428 B2 | 8/2006 | Spillert et al. | |
| 7,179,391 B2 | 2/2007 | Leach et al. | |
| 7,223,346 B2 | 5/2007 | Dorian et al. | |

(Continued)

FOREIGN PATENT DOCUMENTS

EP 0417818 3/1991

(Continued)

OTHER PUBLICATIONS

Al-Waili et al., Hyperbaric oxygen and malignancies: a potential role in radiotherapy, chemotherapy, tumor surgery and phototherapy, Med Sci Monit 11(9):RA279-289 (2005).

(Continued)

*Primary Examiner* — Charles A Marmor, II
*Assistant Examiner* — Carrie Dorna
(74) *Attorney, Agent, or Firm* — Harness, Dickey (57) ABSTRACT

A method of treating irradiated tissue, such as for revascularizing and preventing or reducing wound healing complications in a human or other animal subject having cancer. The method comprises administering to the irradiated tissue a therapeutic composition comprising one or more of platelet rich plasma, platelet poor plasma or platelet concentrate. In some embodiments the complications sought to be prevented and/or reduced can include: fibrotic tissue, prolonged would drainage, hematomas, seromas, fistula formation infection, pain, poor coloration, deficient vascularity, and desensitization in or around the irradiated site.

15 Claims, 5 Drawing Sheets

U.S. PATENT DOCUMENTS

| | | | |
|---|---|---|---|
| 7,374,678 | B2 | 5/2008 | Leach et al. |
| 7,470,371 | B2 | 12/2008 | Dorian et al. |
| 7,553,413 | B2 | 6/2009 | Dorian et al. |
| 7,708,152 | B2 | 5/2010 | Dorian et al. |
| 2002/0082220 | A1 | 6/2002 | Hoemann et al. |
| 2002/0103410 | A1* | 8/2002 | Munro et al. ............ 600/3 |
| 2003/0134892 | A1* | 7/2003 | Dang et al. ............ 514/449 |
| 2003/0198687 | A1 | 10/2003 | Bennett et al. |
| 2003/0205538 | A1 | 11/2003 | Dorian et al. |
| 2004/0182788 | A1 | 9/2004 | Dorian et al. |
| 2004/0182795 | A1 | 9/2004 | Dorian et al. |
| 2004/0185036 | A1 | 9/2004 | Stossel et al. |
| 2004/0251217 | A1* | 12/2004 | Leach et al. ............ 210/787 |
| 2005/0084962 | A1 | 4/2005 | Simon |
| 2005/0109716 | A1 | 5/2005 | Leach et al. |
| 2005/0186120 | A1 | 8/2005 | Dorian et al. |
| 2005/0196874 | A1 | 9/2005 | Dorian et al. |
| 2005/0272644 | A1* | 12/2005 | Chung ............ 514/9 |
| 2006/0034809 | A1 | 2/2006 | Ho et al. |
| 2006/0051865 | A1 | 3/2006 | Higgins et al. |
| 2006/0057693 | A1 | 3/2006 | Simon |
| 2006/0175242 | A1 | 8/2006 | Dorian et al. |
| 2006/0175244 | A1 | 8/2006 | Dorian et al. |
| 2006/0175268 | A1 | 8/2006 | Dorian et al. |
| 2006/0243676 | A1 | 11/2006 | Swift et al. |
| 2006/0273049 | A1 | 12/2006 | Leach et al. |
| 2006/0273050 | A1 | 12/2006 | Higgins et al. |
| 2006/0278588 | A1 | 12/2006 | Woodell-May |
| 2007/0075016 | A1 | 4/2007 | Leach |
| 2007/0092494 | A1 | 4/2007 | Higgins et al. |
| 2007/0184029 | A1* | 8/2007 | Mishra ............ 424/93.7 |
| 2007/0208321 | A1 | 9/2007 | Leach et al. |
| 2008/0011684 | A1 | 1/2008 | Dorian et al. |
| 2008/0193424 | A1 | 8/2008 | McKale et al. |
| 2008/0217263 | A1 | 9/2008 | Higgins et al. |
| 2008/0268064 | A1 | 10/2008 | Woodell-May |
| 2008/0269762 | A1 | 10/2008 | Simon et al. |
| 2008/0283474 | A1 | 11/2008 | Leach et al. |
| 2009/0014391 | A1 | 1/2009 | Leach et al. |
| 2009/0101599 | A1 | 4/2009 | Dorian et al. |
| 2009/0192528 | A1 | 7/2009 | Higgins et al. |
| 2009/0220482 | A1 | 9/2009 | Higgins et al. |
| 2009/0221075 | A1 | 9/2009 | Dorian et al. |
| 2009/0236297 | A1 | 9/2009 | Dorian et al. |
| 2009/0250413 | A1 | 10/2009 | Hoeppner |
| 2009/0253566 | A1 | 10/2009 | Chavarria |
| 2010/0055087 | A1 | 3/2010 | Higgins et al. |

FOREIGN PATENT DOCUMENTS

| | | |
|---|---|---|
| WO | WO 03/088905 | 10/2003 |
| WO | WO 03/092894 | 11/2003 |
| WO | WO 2004/009207 | 1/2004 |
| WO | WO 2008/100442 | 8/2008 |

OTHER PUBLICATIONS

Bielecki et al., Antibacterial effect of autologous platelet gel enriched with growth factors and other active substances, Journal of Bone & Joint Surgery 89-B(3):417-420 (2007).

Francois et al., Human mesenchymal stem cells favour healing of the cutaneous radiation syndrome in a xenogenic transplant model, Ann Hematol 86:1-8 (2007).

Hom et al., Irradiated Soft Tissue and Its Management, Otolaryngologic Clinics of North America 28(5):1003-1019 (1995).

Hom et al., Promoting Healing With Recombinant Human Platelet-Derived Growth Factor-BB in a Previously Irradiated Problem Wound, Laryngoscope 113:1566-1571 (2003).

Milenovic et al., The pectoralis major flap in head and neck reconstruction: First 500 patients, Journal of Cranio-Maxillofacial Surgery 34:340-343 (2006).

Rigotti et al., Clinical Treatment of Radiotherapy Tissue Damage by Lipoaspirate Transplant: A Healing Process Mediated by Adipose-Derived Adult Stem Cells, Plastic and Reconstructive Surgery 119(5):1409-1424 (2007).

Yoo et al., The Use of Autologous Platelet and Plasma in Neck Dissections, Poster session presented at the annual meeting of the American Academy of Otolaryngology—Head and Neck Surgery, Toronto, Ontario, Canada (Sep. 2006).

Biomet Biologics, Inc. "Plasmax Plasma Concentrate" Brochure (2006) 6 pages.

Biomet Biologics, Inc. Vortech Concentration System Product Brochure (Aug. 2005). 16 pages.

Biomet Biologics, Inc. "GPS System Shoulder Recovery with the GPS Platelet Concentrate System" Brochure (2004) 6 pages.

Blanton, Matthew W., M.D. "Adipose Stromal Cells and Platelet-Rich Plasma Therapies Demonstrate Beneficial Healing Properties for Wound Healing" Presentation at Indiana University School of Medicine, May 4, 2006. (9 pages).

DelRossi, Anthony et al. "Platelet-Rich Plasma Reduces Postoperative Blood Loss After Cardiopulmonary Bypass" J Thorac Cardiovasc Surg, vol. 100, Feb. 1990. pp. 281-286.

Eppley, et al., "Platelet Quantification and Growth Factor Analysis from Platelet-Rich Plasma: Implications for Wound Healing," Plastic and Reconstructive Surgery, 114(6):1502-1508 (Nov. 2004).

GPS® II System, "Gravitational Platelet Separation System, Accelerating the Body's Natural Healing Process," Cell Factor Technologies, Inc., Biomet Europe, 16 pages. (2005), http://www.cellfactortech.com/global_products.cfm, printed Sep. 16, 2005.

GPS® II System, "Gravitational Platelet Separation System, User Manual," Cell Factor Technologies, Inc., Biomet Europe, 13 pages [date unknown], http://www.cellfactortech.com/global_products.cfm, printed Sep. 16, 2005.

GPS® System, "GPS® Platelet Concentrate System," Cell Factor Technologies, Inc., Biomet Orthopaedics, Inc., 9 pages (2004).

Harvest Technologies SmartPRep2 Brochure (2002) 9 pages.

Ishida, et al. "Platelet-Rich Plasma With Biodegradable Gelatin Hydrogel Promotes Rabbit Meniscal Tissue Regeneration," 52nd Annual Meeting of the Orthopaedic Research Society Paper No. 1035, 1 page (2006).

Lucarelli, E. et al., Platelet-derived growth factors enhance proliferation of human stromal stem cells, Biomaterials 24:3095-3100 (2003).

Marlovits, S. et al. "A new simplified technique for producing platelet-rich plasma: a short technical note" Eur Spine J, 13 (Suppl. 1), pp. S102-S106 (2004).

Rigotti, Gino et al. "Clinical Treatment of Radiotherapy Tissue Damage by Lipoaspirate Transplant: A Healing Process Mediated by Adipose-Derived Adult Stem Cells" Plast Reconstr Surg, vol. 119, 2007. pp. 1409-1422.

Rubin, J. Peter et al. "Clincial Treatment of Radiotherapy Tissue Damage by Lipoaspirate Transplant: A Healing Process Mediated by Adipose-Derived Adult Stem Cells" Plast Reconstr Surg, vol. 119, No. 5, 2007. pp. 1423-1424.

Swift, Matthew J. "Characterization of Growth Factors in Platelet Rich Plasma" Cell Factor Technologies, Inc. Printed Sep. 16, 2005 from www.cellfactortech.com/global_products.cfm.

The Stone Clinic. "Platelet Rich Plasma (PRP)" May 9, 2006 (1 page).

Toriumi, Dean et al. "Surgical Tissue Adhesives in Otolaryngology—Head and Neck Surgery" Otolaryngologic Clinics of North America, vol. 27, No. 1, Feb. 1994. pp. 203-209.

Woodell-May et al., "Producing Accurate Platelet Counts for Platelet Rich Plasma: Validation of a Hematology Analyzer and Preparation Techniques for Counting," Scientific Foundation, Journal of Carniofacial Surgery 16(5):749-756 (Sep. 2005).

* cited by examiner

METHODS OF REDUCING SURGICAL COMPLICATIONS IN CANCER PATIENTS

CROSS-REFERENCE TO RELATED APPLICATION

This application claims the benefit of U.S. Provisional Application No. 60/917,434 filed May 11, 2007, the disclosure of which is incorporated herein by reference.

BACKGROUND

The present disclosure relates to the administration of therapeutic compositions to cancer surgical sites for the prevention and/or reduction of surgical complications incident to concomitant radiation therapy.

Radiation therapy is a mainstay treatment for cancer, and is used in treating approximately 70% of cancer patients. The therapy itself is responsible for about 40% of cancer cures and is commonly combined with other treatment methods including surgery, chemotherapy and immunotherapy. Nevertheless, radiation induces profound changes in skin and subcutaneous tissues. In general, the severity of radiation induced tissue damage depends on the site of radiation treatment, the type and energy of the radiation dose, and the time-dose volume relationship. These side effects can have particular clinical significance in treatments that involve both radiation and surgery, potentially interfering with healing at the surgical site. Accordingly, therapies that prevent or reduce the side effects of radiation therapy, particularly for surgical candidates or patients, are highly desirable.

SUMMARY

The present technology provides methods for treating irradiated tissue in a human or other animal subject. Included are methods for revascularization and preventing or reducing wound healing complications in a subject having cancer, wherein the subject has an irradiated site and has or will optionally be treated surgically. Complications can include, for example, prolonged wound drainage, hematomas, seromas, fistula formation infection, pain, tissue fibrotic tissue formation, poor coloration, deficient vascularity, and desensitization in the surgical site. Methods comprise administering a blood component to the irradiated site, within a time period after irradiation. Blood components include platelet rich plasma, platelet poor plasma and platelet concentrate.

Further areas of applicability will become apparent from the description provided herein. It should be understood that the description and specific examples are intended for purposes of illustration only and are not intended to limit the scope of the present disclosure.

DRAWINGS

The present technology will become more fully understood from the detailed description and the accompanying drawings, wherein.

DETAILED DESCRIPTION

The following description of technology is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom.

Figure 1:
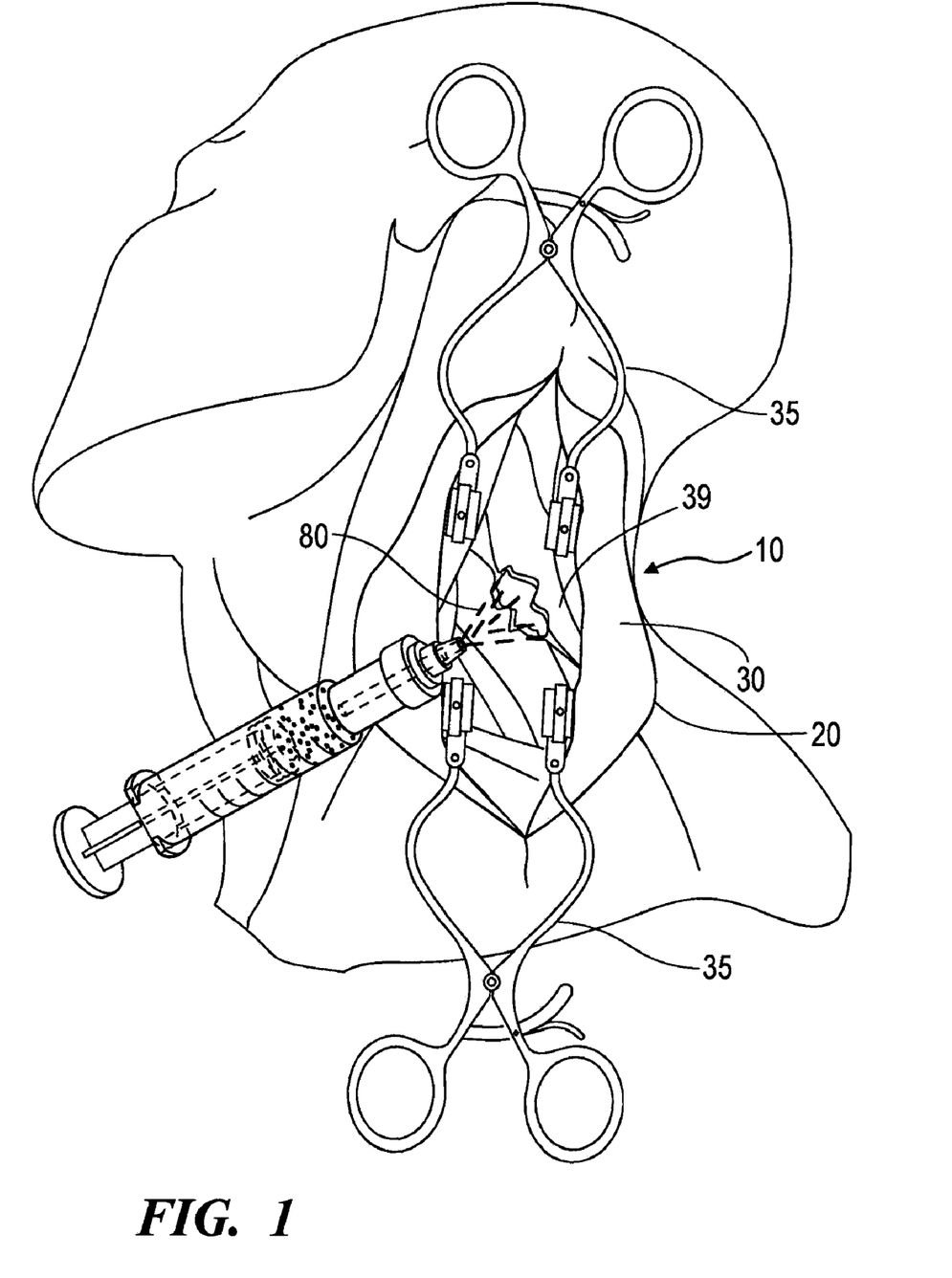
FIG. 1 illustrates a representative site of a tissue defect on a subject in need of treatment according to one embodiment of the present technology.

FIG. 1 illustrates irradiated tissue 39, in a surgical site 10 in a limb of a human patient having a cancer. It should be understood, however, that such tissue can be at any place on the body of a cancer patient who has received radiation therapy, and that such therapy may be performed without surgery, or before or after surgery. As discussed further below, a surgical site comprises any breach of skin and can include any incision or wound involving hard or soft tissue, such as skin, fascia, muscle, viscera, organs or bone. The surgical site can comprise the site of dissection of skin, cutaneous tissue, muscle and other tissues to expose a tumor to be removed, and can include a site where a tumor has been removed and tissue is repaired or reconstructed that is cosmetically or physiologically inadequate incident to a cancerous tumor. For example, as shown in FIG. 1, a surgical site 10 can include an incision of skin 20, connective tissues (superficial fascia tissue 30), and tissue 39 (e.g., muscle tissue) which has been irradiated in a method of this technology.

Figure 2:
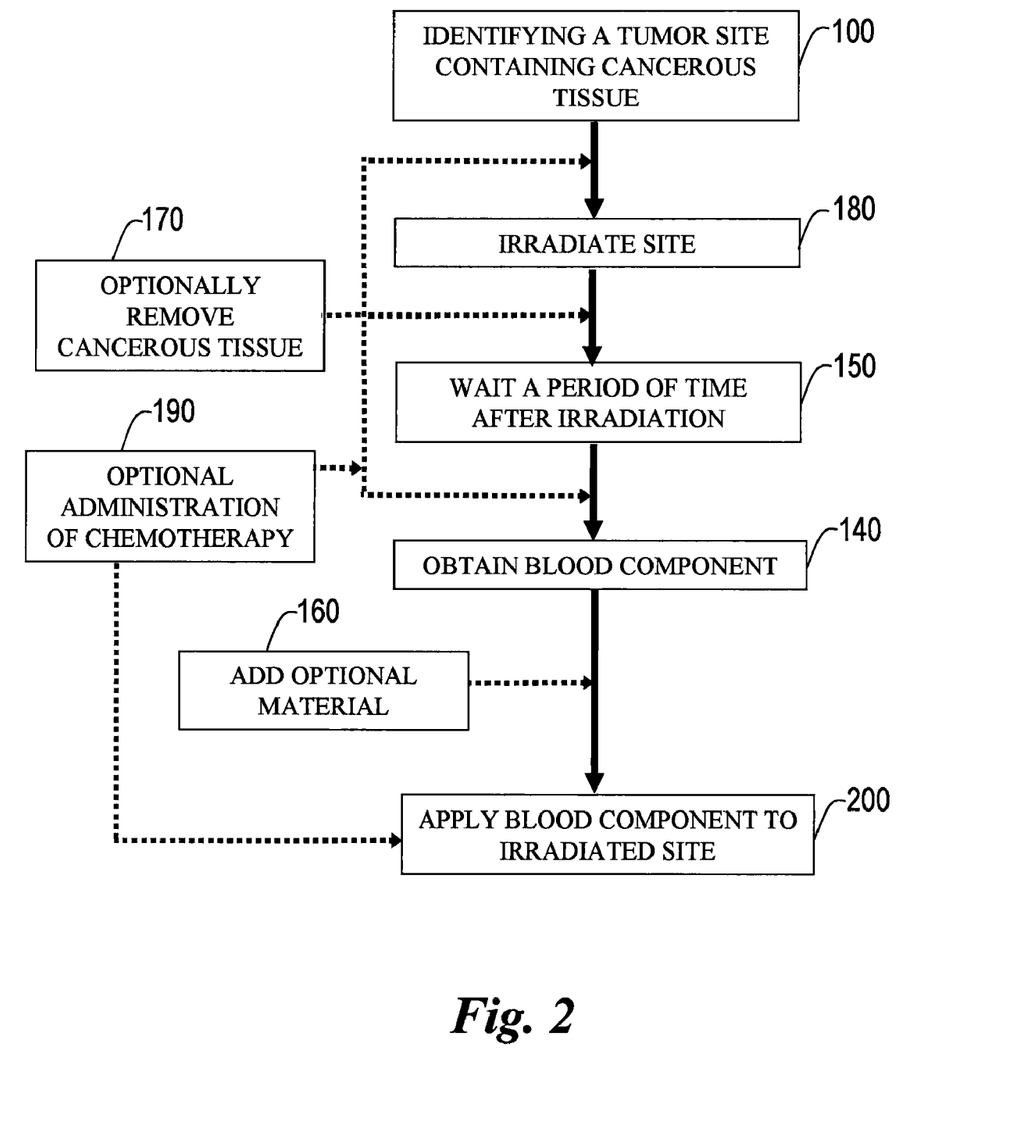
FIG. 2 is a diagrammatic illustration of a representative method for treating irradiated tissue according to one embodiment of the present technology.

One general method for treating irradiated tissue in a human or other animal subject is shown in FIG. 2. In summary, a tumor site is identified containing cancerous cells or tissue at step 100. Tissue comprising the cancerous tissue is then irradiated at step 180. After a waiting period 150, a blood component is obtained at step 140. Optional materials may be added to the blood component at step 160. The blood component is then applied to the irradiated tissue at step 200. The methods may comprise several optional steps. For example, cancerous tissue may be removed by surgery at step 170. Such surgery may be performed before or after (or both) the irradiation step 180. One or more chemotherapeutic agents may also be administered to the subject in step 190 before, after, or during any or all of steps 170, 180, 150, and 200. Moreover, the radiation step 180 and administration of chemotherapeutic agent step 190 may be repeated two or more times.

As generally discussed above, a site containing cancerous tissue is identified at step 100. Such cancerous tissue can occur anywhere in the subject. Examples include tumors in breast, head and neck tissues. Identifying the tumor site can be achieved using any medically acceptable procedure including invasive and non-invasive screening techniques. Invasive screening techniques used to identify a tumor site can include tissue biopsy, laparotomy and laparoscopy. Non-invasive screening techniques include manual examination, palpitation, computer tomography scanning (CT scanning), magnetic resonance imaging (MRI), and x-rays.

Referring to FIG. 2, radiation is applied to tissue comprising the tumor site in the irradiation step 180. The form of the irradiation procedure can include focused tissue irradiation, steriotactic irradiation, whole beam irradiation, and brachytherapy. The specific radiation type, level, and dosage regimen is determined according to the type, size and location of cancer to be treated and general health of the subject, pursuant to sound medical practice.

As further depicted in FIG. 2, a blood component is obtained at step 140 and applied to irradiated tissue at step 200. Preferably, however, there is a waiting period 150 prior to applying the blood component in step 200. The timing of the waiting period step 150 after irradiation step 180 may affect the wound healing process and the repair of the irradiated tissue. In some embodiments, the waiting period 150 after the irradiation step 180 may be as short as 3 weeks, In some embodiments, for example for head and neck tumors, a suitable waiting period can include 1 month to 7 months before subsequent treatment with blood components of step 200. In breast cancers, a waiting period can be shorter, for example 1 month to 5 months before subsequent application of blood components in step 200.

As discussed above, a blood component is obtained at step 140. The blood component may be obtained from blood from the subject to be treated, or from another human or animal donor identified as being compatible with the subject. The blood component may comprise fractionated plasma in the form of platelet-rich plasma, platelet-poor plasma, or concentrated platelet-poor plasma. In this regard, a blood component comprising platelet-rich plasma may have an increased concentration of platelets relative to whole blood, and in some embodiments, the platelet concentration can be from about 3-fold to about 10-fold greater than the platelet concentration in whole blood. A blood component comprising platelet-poor plasma may have a decreased concentration of platelets relative to whole blood, and in some embodiments, the platelet concentration can be from about 0 to about 100,000 platelets/mL. The platelet-poor plasma can also be concentrated to make concentrated platelet-poor plasma. Further, the isolated tissue composition obtained at step 140 may have varying mixtures of platelet-rich plasma and platelet-poor plasma, or isolated platelets resuspended with platelet-poor plasma or concentrated platelet-poor plasma, resulting in a range of platelet concentrations.

A blood component can be obtained at step 140 by one or more methods, including filtration, cryoprecipitation, and density fractionation. Density fractionation techniques include single stage centrifugation, centrifugation in multiple stages, and continuous flow centrifugation.

Figure 3:
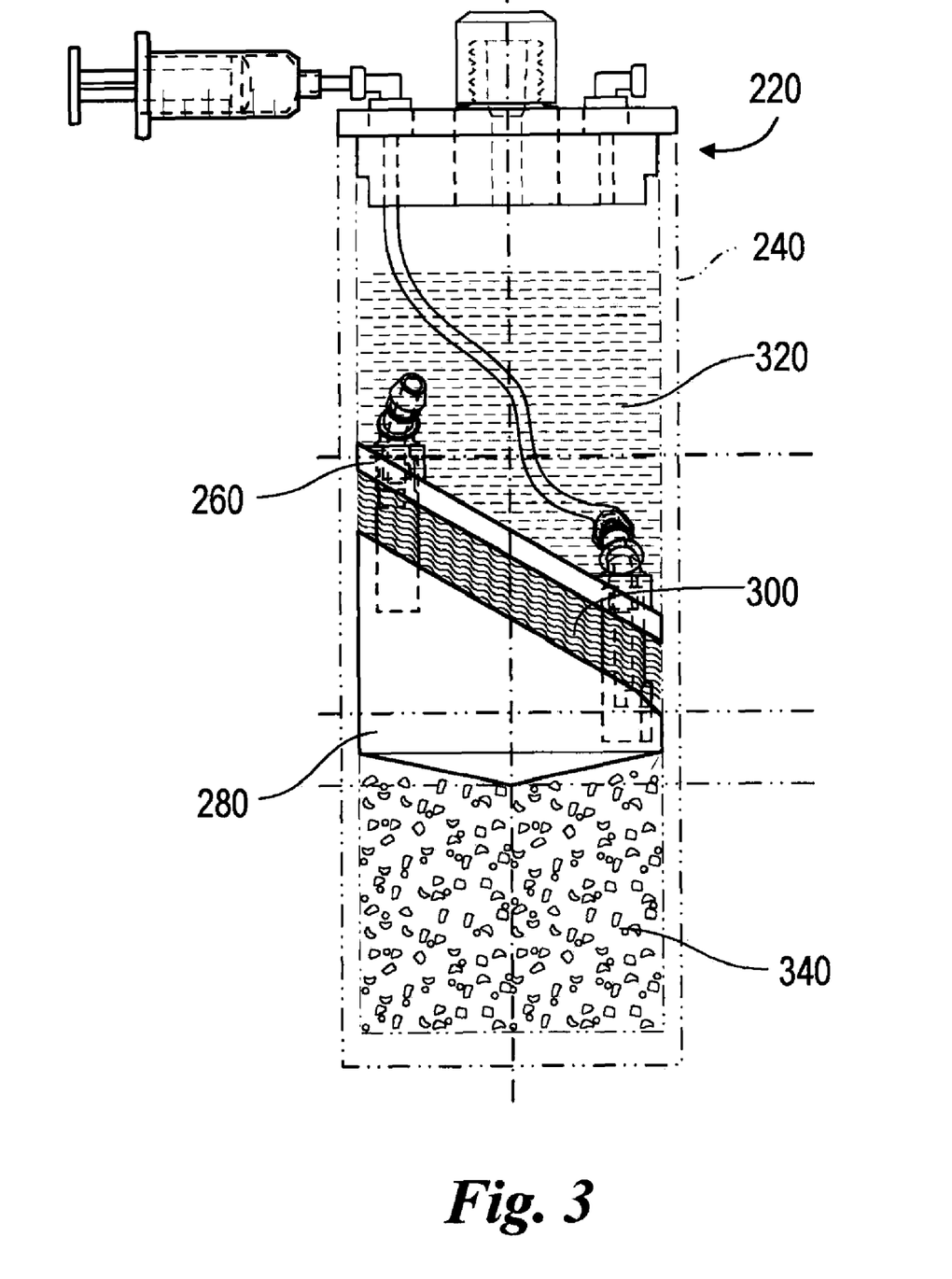
FIG. 3 is a cross-sectional view of a representative device used for isolating a blood component according to one embodiment of the present technology.

One example of a device that may be used for forming the blood component by density fractionation at step 140 is shown in FIG. 3. In this regard, the device 220 includes a container 240, such as a tube, that is placed in a centrifuge after being filled with blood. The container 240 includes a buoy system having an isolator 260 and a buoy 280. The buoy 280 has a selected density, which is tuned to reach a selected equilibrium position upon centrifugation; this position lies between a more dense blood fraction and a less dense blood fraction. During centrifugation, the buoy 280 separates the blood within the container 240 into at least two fractions, without substantially commingling the fractions, by sedimenting to a position between the two fractions. In this regard, the isolator 260 and the buoy 280 define a layer comprising platelet-rich plasma 300, while less dense platelet-poor plasma 320 generally fractionates above the isolator 260, and more dense red blood cells 340 generally fractionate below the buoy 280. Following centrifugation, a syringe or tube may then be interconnected with a portion of the buoy system to extract one or more selected fractions for use as the blood component. Devices including those disclosed in FIG. 3 and associated methods are described in U.S. Patent Application Publication 2004/0251217, Leach et al., published Dec. 16, 2004; and U.S. Patent Application Publication 2005/0109716, Leach et al., published May 26, 2005; both of which are incorporated by reference herein. One such device that is commercially available is the GPS™ Platelet Concentrate System, from Biomet Biologics, Inc. (Warsaw, Ind.).

Another example of a device that may be used in step 140 to isolate platelet-rich plasma by density fractionation comprises a centrifugal drum separator and an erythrocyte capture trap. In one embodiment, the walls of the centrifugal drum separator are coated with a depth filter having pores and passageways that are sized to receive and entrap erythrocytes. Blood is placed in the centrifugal drum, and the drum is spun along its axis at sufficient speed so as to force erythrocytes from the blood into the depth filter. After spinning, the erythrocytes remain in the filter and the remaining platelet-rich plasma is extracted. The platelet-rich plasma may be concentrated by desiccation. Such concentration devices include the VORTECH® Concentration System (Biomet Biologics, Inc., Warsaw, Ind.), and are disclosed in U.S. Patent Application Publication 2006/0175244, Dorian et al., published Aug. 10, 2006; and U.S. Patent Application Publication 2006/0175242, Dorian et al., published Aug. 10, 2006; both of which are hereby incorporated by reference. Such devices may be used to prepare platelet-rich plasma in lieu of or in addition to using the tube having a buoy that is described above and shown in FIG. 3.

Figure 4A:
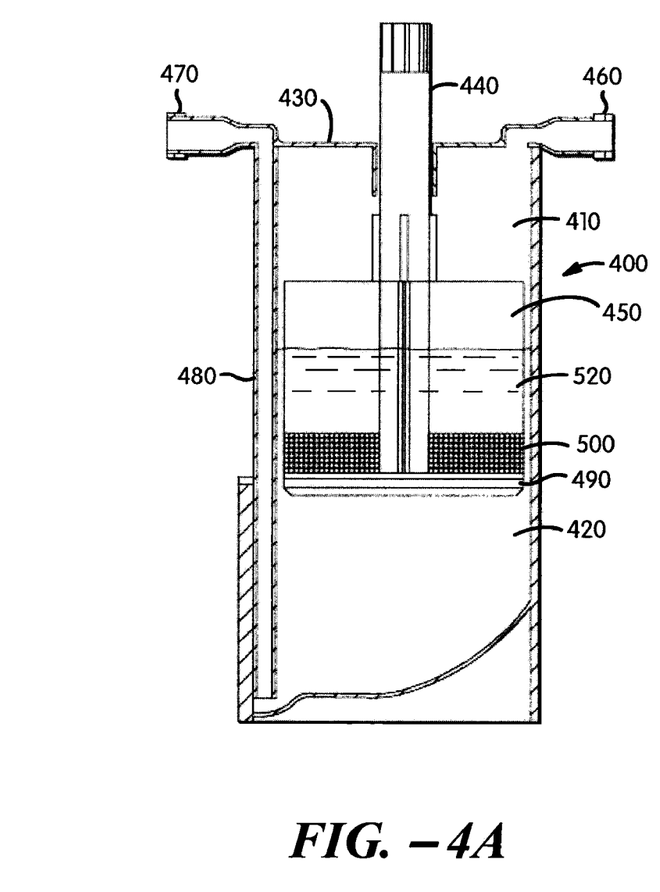
FIGS. 4A and 4B are cross-sectional views of a representative device used for concentrating a blood component according to one embodiment of the present technology.
Figure 4B:
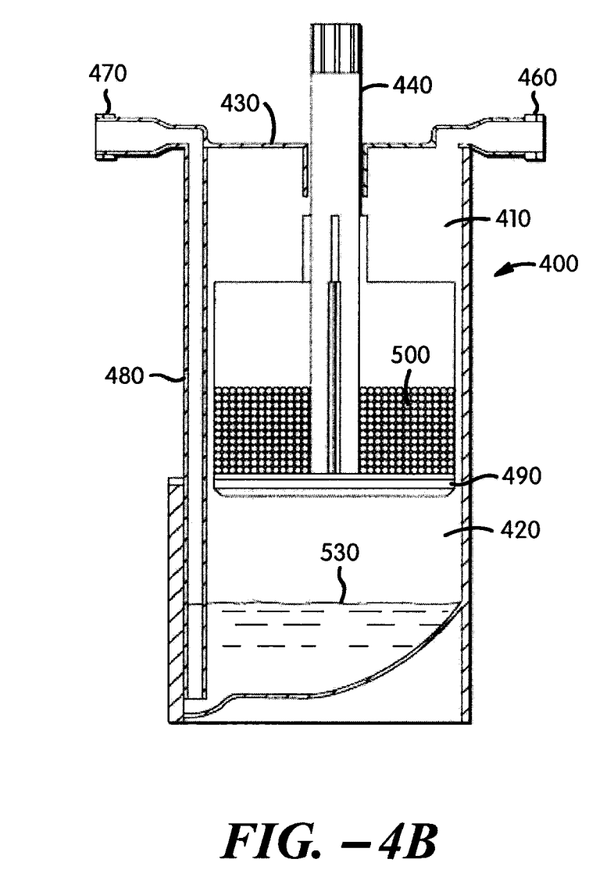

A concentrated blood component, such as concentrated platelet-poor plasma, may also be obtained at step 140. Platelet-poor plasma can be obtained, for example, using a device illustrated in FIG. 3, as described above. The platelet-poor plasma is then concentrated using any of a variety of concentration methods, including those known in the art for reducing the water content of the plasma. One example of a device that may be used for forming concentrated platelet-poor plasma at step 140 is shown in FIGS. 4A and 4B. In this regard, the device 400 has an upper chamber 410 and a lower chamber 420. The upper chamber 410 has an end wall 430 through which the agitator stem 440 of a gel bead agitator 450 extends. The device 400 also has a plasma inlet port 460 that extends through the end wall 43 and into the upper chamber 410. The device 400 also includes a plasma concentrate outlet port 470 that communicates with a plasma concentrate conduit 480. The floor of upper chamber 410 includes a filter 490, the upper surface of which supports desiccated concentrating polyacrylamide beads 500.

During use, blood plasma 520 (preferably cell free) is initially introduced into the upper chamber 410 through the plasma inlet port 460. The blood plasma 520 entering the upper chamber 410 flows to the bottom of the chamber where it contacts the polyacrylamide beads 500 as shown in FIG. 4A. As the polyacrylamide beads 500 remove water from blood plasma 520, the plasma proteins are concentrated. During this concentration stage, the plasma and its components can be concentrated to a concentration from about 1.5 to about 3 times or higher than its original concentration.

Referring to FIG. 4B, the device 400 is then placed in the cup receptors of a conventional laboratory centrifuge (not shown) and spun at a speed that will create a centrifugal force that will remove plasma concentrate 530 from the polyacrylamide beads 500, and cause the plasma concentrate 530 to flow through the filter 490. The filter 490 can be constructed to allow flow of liquid there through at centrifugal forces above 10×g. After centrifugation is completed, the device 400 is removed from the centrifuge. The plasma concentrate 530 is then drawn from lower chamber 420 through plasma concentrate conduit 480 to the plasma concentrate outlet port 470.

Exemplary plasma concentration devices useful in step 140 are disclosed in U.S. Patent Application Publication 2006/0175268, Dorian et al., published Aug. 10, 2006; and U.S. Patent Application Publication 2006/0243676, Swift et al., published Nov. 2, 2006; both of which are incorporated by reference herein. Such a plasma concertration device is commercially available as PLASMAX® Plus Plasma Concentrator, from Biomet Biologics, Inc. (Warsaw, Ind.).

Other devices that may be used to obtain the isolated tissue composition at step 140 are described, for example, in U.S. Pat. No. 6,398,972, Blasetti et al., issued Jun. 4, 2002; U.S. Pat. No. 6,649,072, Brandt et al., issued Nov. 18, 2003; U.S. Pat. No. 6,790,371, Dolecek, issued Sep. 14, 2004; and U.S. Pat. No. 7,011,852, Sukavaneshvar et al., issued Mar. 14, 2006; and U.S. Patent Application Publication 2005/0196874, Dorian et al., published Sep. 8, 2005. In addition to the concentration devices GPS® Platelet Concentrate System and VORTECH® Concentration System, other commercially available devices that may be used to obtain the isolated tissue composition at step 14 include the platelet seperation devices MEGELLAN® Autologous Platelet Separator System, commercially available from Medtronic, Inc. (Minneapolis, Minn.); SMARTPREP®, Platelet Concentrate System, commercially available from Harvest Technologies Corporation (Plymouth, Mass.) and DePuy Spine, Inc. (Warsaw, Ind.); the AUTOLOGEL™ Process, commercially available from Cytomedix (Rockville, Md.), and the GENESISCS™ component concentrating system, available from EmCyte Corporation (Fort Myers, Fla.).

The blood component obtained in step 140 may be combined with one or more optional materials in step 160. Such optional materials include, for example, platelet activators, scaffolds, bioactive materials, cytokines, and combinations thereof. The optional materials can be applied in step 160 just prior to the administration of the blood component in step 200. Alternatively, the optional materials may be applied in step 160 concomitant with administration of the blood component in step 200, or following administration of the blood component to the surgical site in step 200.

Platelet activators may be added in step 160 so as to activate one or more growth factors within platelets contained in an isolated tissue composition. In this regard, the platelet activator may serve to activate one or more growth factors within platelets contained in the blood component. Activation of the platelets by the platelet activators can be performed just prior to administration of the blood component, concomitant with administration of the blood component, or following administration of the blood component to the site. Platelet activators among those useful herein include thrombin, including autologous thrombin, calcium chloride ($CaCl_2$), and mixtures thereof. In some embodiments, coagulation factors can be used to activate platelets. Coagulation factors include, but are not limited to, one or more of the following: V, VII, VIIa, IX, IXaβ, X, Xa, XI, XIa, XII, α-XIIa, β-XIIa, and XIII. Various embodiments can include one or more coagulation factors, including autologous coagulation factors, and/or thrombin, and/or $CaCl_2$.

A scaffold may be added in step 160 to contain, support, or retain the blood component at the surgical site, or to facilitate migration of endogenous cells into the surgical site. Scaffolds may be formed from porous or semi-porous, natural, synthetic or semisynthetic materials. Scaffold materials include those selected from the group consisting of bone (including cortical and cancellous bone), demineralized bone, ceramics, polymers, and combinations thereof. Bone, demineralized bone and ceramics may be particularly useful in methods where the blood component is applied to bone. Suitable polymers may include collagen, including lyophilized or skin-derived collagen as disclosed in U.S. Application Publication No. 2007/0092494, Higgins, published Apr. 26, 2007, which is incorporated by reference herein. Polymers may also include gelatin, hyaluronic acid, chitosan, polyglycolic acid, polylactic acid, polypropylenefumarate, polyethylene glycol, and copolymers or combinations thereof. Ceramics include any of a variety of ceramic materials known in the art for use for implanting in bone, such as calcium phosphate (including tricalcium phosphate, tetracalcium phosphate, hydroxyapatite, and mixtures thereof). Ceramics useful herein include those described in U.S. Pat. No. 6,323,146, Pugh et al., issued Nov. 27, 2001; and U.S. Pat. No. 6,585,992, Pugh et al., issued Jul. 1, 2003; both of which are incorporated by reference herein. A commercially available bone implant ceramic is PROOSTEON® from Interpore Cross International, Inc. (Irvine, Calif.).

In some embodiments, step 160 may also include the addition of one or more bioactive materials that provide a therapeutic, nutritional or cosmetic benefit to the subject in which implants are applied. Such benefits may include repairing unhealthy or damaged tissue, minimizing infection at the surgical site, increasing integration of healthy tissue into the surgical site, and preventing disease or defects in healthy or damaged tissue.

Bioactive materials that may be included in step 160 include organic molecules, proteins, peptides, peptidomimetics, nucleic acids, nucleoproteins, antisense molecules, polysaccharides, glycoproteins, lipoproteins, carbohydrates, and polysaccharides; synthetic and biologically engineered analogs thereof; living cells such as chondrocytes, bone marrow cells, stem cells, viruses and virus particles, natural extracts, and stromal cells; and combinations thereof. Specific non-limiting examples of bioactive materials include cytokines, hormones, antibiotics and other anti-infective agents, hematopoietics, thrombopoietics agents, antiviral agents, antitumoral agents (chemotherapeutic agents), antipyretics, analgesics, anti-inflammatory agents, enzymes, vaccines, immunological agents and adjuvants, cytokines, growth factors, cellular attractants and attachment agents, gene regulators, vitamins, minerals and other nutritionals, platelet activators, and combinations thereof. Bioactive agents may be included that have effects at sites not proximate to the surgical site, such as (in addition to agents listed above) hematopoietics, thrombopoietics, antidementia agents, antiallergic agents, antidepressants, psychotropic agents, antiparkinsonian agents, therapeutic agents for osteoporosis, cardiotonics, antiarrythmic agents, vasodilators, antihypertensive agents, diuretics, anti-cholinergic, antidiabetic agents, cholesterol lowering agents, gastrointestinal agents, muscle relaxants, and combinations thereof.

Step 160 may also include the addition of one or more cytokines, including isolated, synthetic or recombinant molecules. Cytokines useful herein include growth factors such as transforming growth factor (TGF-beta), bone morphogenic proteins (BMP, BMP-2, BMP-4, BMP-6, and BMP-7), neurotrophins (NGF, BDNF, and NT3), fibroblast growth factor (FGF), granulocyte-colony stimulating factor (G-CSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF-8), growth differentiation factor-9 (GDF9), basic fibroblast growth factor (bFGF or FGF2), vascular endothelial growth factor (VEGF), epidermal growth factor (EGF), insulin-like growth factors (IGF-I, IFG-II), and combinations thereof. Cytokines can be applied to the site just prior to the administration of the therapeutic composition, concomitant with administration of the therapeutic composition, or following administration of the therapeutic composition to the subject.

Stem cells, such as bone marrow-derived stem cells and adipose-derived stromal cells, may also be added to the blood component in step 160. Adipose-derived stromal cells may be obtained from processing of lipid tissue by standard liposuction and lipoaspiration methods known in the art. Adipose tissue may be treated with digestive enzymes and with chelating agents that weaken the connections between neighboring cells, making it possible to disperse the tissue into a suspension of individual cells without appreciable cell breakage. Following disaggregation, the adipose stromal cells may be isolated from the suspension of cells and disaggregated tissue. A device as shown in FIG. 3, such as the GPS™ Platelet Concentrate System, may be used to isolate adipose stromal cells.

Figure 5:
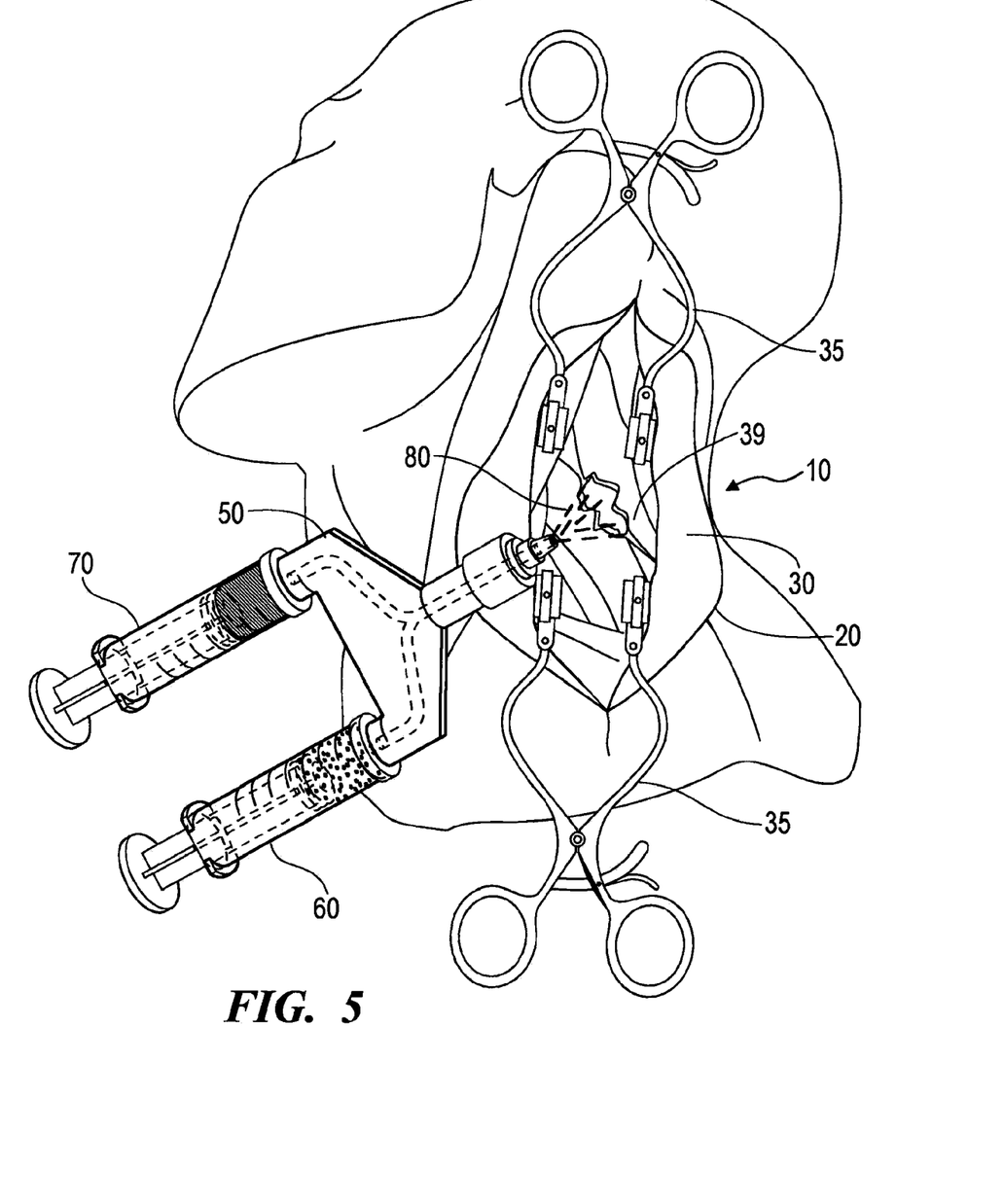
FIG. 5 illustrates a representative manner of administering a therapeutic composition to a subject according to one embodiment of the present technology.

Referring again to FIG. 2, the blood component obtained at step 140 is administered to the irradiated site at step 200. For example, the blood component obtained in step 140 can be sprayed onto the irradiated tissue 39 using an applicator 50, as shown in FIG. 5. The blood component may be administered using any medically acceptable process or procedure by which the blood component is implanted, injected, sprayed, applied, or otherwise administered in, on, or in proximity to the site of the irradiated site so as prevent or reduce surgical complications, for example fibrotic tissue formation. Methods of treating an irradiated site may include applying the blood component to an irradiated site to facilitate or enhance the rate of healing and/or provide for more complete healing, prevent wound healing complications, or reduce the number and severity of surgical complications. For example, the blood component may be effective in preventing or reducing wound healing complications in cancer patients after irradiation of the tumor site by inducing homeostasis, stimulating soft tissue and bone healing, enhancing skin graft adherence, increasing bone graft union, increasing antimicrobial effects, and promoting angiogenesis and vascularity in the irradiated site.

Administration of the blood component in step 200 can comprise single or multiple applications in a regular or irregular pattern in and surrounding the site of the irradiation. As shown in FIG. 5, a combination of platelet-rich plasma in a first syringe 60 may be admixed with platelet-poor plasma and thrombin in a second syringe 70 upon application into the irradiated tissue 39. For example, the mixture 80 is sprayed on to the surface of the tissues within a surgical site 10 exposed by retractors 35 after a tumor has been removed.

In some embodiments, solid support including a membrane, a cloth, a tampon, or gauze can be implanted into the irradiated site and co administered with the blood component in step 200. In some embodiments, the solid support can be coated or imbibed with the therapeutic composition before implantation into the irradiated site.

Step 200 may also include the application of a fibrin sealant or glue into the irradiated site revascularize damaged blood vessels and/or prevent the formation of fibrotic tissue at the irradiated site. In various embodiments, the blood component can include platelet poor plasma that is naturally enriched with fibrinogen. In some embodiments, the administration of the blood component in step 200 can be accomplished by injecting the blood component into the irradiated site. With reference to FIG. 5, in some embodiments, an applicator 50 may combine platelet rich plasma contained in a first syringe 60 and mixture of CaCl and platelet poor plasma in a second syringe 70. In some embodiments, the platelet poor plasma in the second syringe 70 is also admixed with thrombin and applied through the applicator 50. The amount of fibrin glue can be tailored to the status of the irradiated site. In some embodiments, when there is a high degree of bleeding in the irradiated site, for example after cancerous tissue removal of step 170, the therapeutic composition can contain a higher percentage of platelet poor plasma or platelet poor plasma concentrate and thrombin to assist in hemostasis. Where there is a significant amount of blood or other fluid at the site, the fluid will activate the interaction of fibrinogen and thrombin. Fibrin glues can be particularly useful where other suturing techniques, such as stitching or stapling, are unsuitable. They can be placed directly into the irradiated site, and are fully reabsorbed into the body.

Referring again to FIG. 2, surgical removal of cancerous tissue is optionally performed in step 170. Such surgery may be performed at one or more times throughout the treatment process, and may be before or after the irradiation step 180. Surgical procedures include any diagnostic, or curative procedure during which an incision is made in soft or hard tissue.

Curative surgery is typically performed when a tumor appears to be confined to one area and it is likely that all of the tumor can be removed. Curative surgery can be the primary treatment of the cancer. In the removal of certain soft tissue sarcomas, the tumor mass is excised and replacement of tissue is done by implanting an autologous region of compatible tissue, such as muscle and/or a myocutaneous tissue flap. Debulking surgery may be performed to remove a portion of a tumor when removing the entire tumor would cause too much damage to an organ or near-by tissues. In these cases, the surgeon may remove as much of the tumor as possible and then treat the remaining tumor with radiation therapy and/or chemotherapy. Palliative surgery may be performed to treat complications of advanced cancer. Rather than curing the cancer, palliative surgery may correct a problem that is causing discomfort or disability. For example, some cancers in the abdomen may grow large enough to obstruct (block off) the intestine. This may require surgery to remove the blockage. Palliative surgery may also be used to treat pain when it is hard to control it by other means. Supportive surgery may also be performed to augment other types of treatment. For example, a vascular access device such as a catheter port can be surgically placed into a large vein. The port can then be used to give chemotherapy treatments or draw blood for testing, reducing the number of needle sticks needed. Other supportive surgeries can include ligament and tendon repair when removal of primary tumor mass necessitates removal of healthy tissue. Occasionally, the patient may also require a surgical procedure necessitated for reasons unrelated to the tumor itself.

In some methods, the cancerous tissue in the neck area is ressected using surgical procedures, such as salvage neck dissection, radical neck dissection, dissection of the oropharynx, salvage neck dissection, modified radical neck dissection, extended radical neck dissection, elective neck dissections, supraomohyoid neck dissection, anterior compartment neck dissection, posterolateral neck dissection, lateral neck dissection.

Chemotherapy may also be performed, in step 190. Chemotherapy may employ topical or systemic administration of one or more antineoplastic agents including those well known in the art. The specific selection and dosage regimen for such agents is determined according to the type and location of cancer treated and the general health of the subject pursuant to sound medical practice. The chemotherapy administration step 190 can be performed before, after, or during any or all of steps 150, 170, 180, and 200.

As mentioned above, the present technology also provides methods for reducing one or more complications of tissue irradiation. Such complications include fistulas, fibrosis, seromas, hematomas, infections, discoloration of the skin, wound pain, wound dehiscence, wound breakout, fibrotic tissue formation and necrosis in and around the irradiated site and other areas affected by the irradiation. The severity of the complications can be measured quantitatively and qualitatively, for example, the length of stay in the hospital, the amount of wound drainage produced, reduction in the elasticity of the tissue around the surgical site, degree of scar formation, degree of tissue adhesion between the incision site or between donor tissue implanted in the surgical bed and surrounding treated tissue, vascular deficiency and loss of sensitization around the surgical site.

The following non-limiting example illustrates the materials, methods, and processes of the present technology. The example is provided for illustrative purposes of how to make and use the materials and methods of this technology and is not intended to be a representation that given embodiments of this technology have, or have not, been performed or tested.

EXAMPLE

A method of the present technology is performed on a human subject undergoing salvage neck dissection for cervical metastases. Patients undergoing such salvage neck dissections are generally a higher risk for surgical complications including neck fibrosis, prolonged wound drainage, and poor tissue adhesion resulting in delayed wound healing. In the method, blood is obtained from the subject and placed in a centrifuge tube as depicted in FIG. 3, and spun in a GPS™ Platelet Concentrate System, from Biomet Biologics, Inc. (Warsaw, Ind.). A blood component comprising platelet-rich plasma is obtained, and applied to the surgical bed. A drain with a 2-layer closure was implanted during the procedure, to allow wound drainage.

Post-operatively, the drainage from the surgical site is measured to be about 264 ml, which is observed to be less than the drainage from the surgical sites of similar subjects who are not treated with a method of the present technology. The subject is released from the hospital in about 3 days, which is less than the hospital stay from similar subjects who are not treated with a method of the present technology. Neck skin fibrosis is also measured by a fibrosis measurement device commercially available as CUTOMETER® MPA 580 (skin probe), and found to be less than that measured in similar subjects who are not treated with a method of the present technology.

The embodiments and the examples described herein are exemplary and not intended to be limiting in describing the full scope of the devices, compositions and methods of the present technology. Equivalent changes, modifications and variations can be made within the scope of the present technology, with substantially similar results.

What is claimed is:

1. A method for treating irradiated tissue in a human or other animal subject, the method comprising:
   identifying cancerous tissue in the subject;
   irradiating tissue comprising the cancerous tissue, forming irradiated tissue in the subject;
   waiting for a period of time after the irradiating, wherein the period of time is from about 1 month to about 7 months;
   surgically removing the cancerous tissue after the wait period; and
   administering a blood component selected from the group consisting of platelet rich plasma, platelet poor plasma, concentrated platelet poor plasma, platelet concentrate and mixtures thereof to the irradiated tissue in the subject after the surgically removing of cancerous tissue.

2. A method according to claim 1, wherein the cancerous tissue is in the head or neck.

3. A method according to claim 2, wherein the cancerous tissue site is in the neck and the surgically removing comprises neck dissection selected from the group consisting of salvage neck dissection, radical neck dissection, dissection of the oropharynx, modified radical neck dissection, extended radical neck dissection, elective neck dissections, supraomohyoid neck dissection, anterior compartment neck dissection, posterolateral neck dissection, and lateral neck dissection.

4. A method according to claim 2, wherein the cancerous tissue is in the head and the surgically removing comprises a head dissection of the tissue.

5. A method according to claim 1, wherein the cancerous tissue is in a breast.

6. A method according to claim 1, wherein the irradiating is performed with two or more doses of radiation administered to the tumor site within a period of 3 months or less.

7. A method according to claim 1, wherein the blood component is administered in an amount sufficient to reduce one or more complications comprising prolonged wound drainage, hematomas, seromas, fistula formation, infection, pain, fibrotic growth, poor coloration, and desensitization.

8. A method according to claim 1, wherein the blood component is administered in an amount effective to increase vascularization of the irradiated tissue.

9. The method according to claim 1, wherein the blood component is administered in an amount effective to reduce fibrotic growth in the irradiated tissue.

10. The method according to claim 1, wherein the administering comprises administering the blood component to irradiated tissue proximate to the site of the cancerous tissue.

11. The method according to claim 1 further comprising:
   a. obtaining blood compatible with the subject; and
   b. fractionating the blood to produce the blood component, wherein the blood component is selected from the group consisting of platelet rich plasma and platelet poor plasma.

12. The method according to claim 11, wherein the fractionating comprises centrifuging the blood in a container including a buoy that is able to separate the blood into two or more fractions having different densities.

13. The method according to claim 1, further comprising administering to the irradiated tissue an optional material selected from the group consisting of platelet activators, scaffolds, bioactive materials, cytokines, and combinations thereof.

14. The method according to claim 13 wherein the optional material is a platelet activator selected from the group consisting of thrombin, autologous thrombin, $CaCl_2$, a coagulation factor, or combinations thereof.

15. A method according to claim 13 comprising administering an antineoplastic agent to the subject.

* * * * *